US005618982A

United States Patent [19]
Gilbert et al.

[11] Patent Number: 5,618,982
[45] Date of Patent: Apr. 8, 1997

[54] CATALYTIC C-ALKYLATION OF KETONES

[75] Inventors: Laurent Gilbert; Michel Spagnol, both of Lyons, France

[73] Assignee: Rhone-Poulenc Chimie, Courbevoie Cedex, France

[21] Appl. No.: 346,226

[22] Filed: Nov. 22, 1994

[30] Foreign Application Priority Data

Nov. 22, 1993 [FR] France ................... 93 13920

[51] Int. Cl.$^6$ ................... C07C 45/45
[52] U.S. Cl. .......... 568/346; 568/347; 568/314; 568/315; 568/388; 568/391
[58] Field of Search ............. 568/314, 315, 568/346, 347, 388, 391

[56] References Cited

U.S. PATENT DOCUMENTS

| | | | |
|---|---|---|---|
| 2,549,520 | 4/1951 | Prichard | 568/314 |
| 3,932,518 | 1/1976 | Arpe | 568/347 |
| 4,567,005 | 1/1986 | Woo | 568/388 |
| 4,618,725 | 10/1986 | Levy | 568/347 |

FOREIGN PATENT DOCUMENTS

| | | | |
|---|---|---|---|
| 0166490 | 1/1986 | European Pat. Off. | 568/346 |
| 0194591 | 9/1986 | European Pat. Off. | 568/340 |
| 1448855 | 9/1976 | United Kingdom | 568/346 |

*Primary Examiner*—James H. Reamer
*Attorney, Agent, or Firm*—Burns, Doane, Swecker & Mathis, L.L.P.

[57] ABSTRACT

Ketones having at least one hydrogen atom or ester group in the α-position with respect to a ketonic carbonyl group thereof, for example cyclopentanone, 2-methylcyclopentanone and other substituted cyclopentanones, are effectively C- or α-alkylated, especially on an industrial scale, by reacting same with an alkylating agent in the presence of a catalytically effective amount of a condensed or uncondensed orthophosphate anion.

56 Claims, No Drawings

CATALYTIC C-ALKYLATION OF KETONES

BACKGROUND OF THE INVENTION

1. Field of the Invention

The present invention relates to the C-alkylation of ketones, and, more especially, to the catalytic C-alkylation of acyclic or cyclic ketones containing at least one hydrogen atom or an ester group in the α-position with respect to a carbonyl group thereof.

Preferred reactant compounds for C-alkylation according to this invention include cyclopentanone, 2-methylcyclopentanone and other substituted cyclopentanones.

2. Description of the Prior Art

Ketone alkylation processes are known to this art wherein the hydrogen atom in the α-position with respect to the carbonyl group is alkylated.

Conventional processes entail transforming the ketone function into an enolate by treatment with a base, then reacting the enolate thus formed with an alkylating agent. This technique is described in Jean D'Angelo, *Tetrahedron*, 32, pp. 2979–2990 (1976). The enolate is formed by reacting the ketone with a base such as $iPr_2NLi$, at low temperature (−78° C.), in a suitable polar aprotic solvent, for example THF.

This process cannot be carried out on an industrial scale; the presence of the base causes the formation of salts which must then be eliminated.

G. Storck et al, *J. Am. Chem. Soc.*, 85, pp. 207–216 (1983) describes the alkylation of carbonyl compounds by conversion into an intermediate enamine which reacts with the alkylating agent to produce an imine which is subsequently hydrolyzed. The alkylation process is very complex because of the large number of steps involved.

Z. Jedlinski et al, *Synlett*, pp. 213, (1990), describes an equally complicated alkylation process. In such process, an enolate intermediate is formed by reacting a cyclic ketone with a base which is a complex of potassium and 18-C-6 crown ether in THF. The ketone enolate thus obtained reacts with the alkylating agent to produce the α-alkylated ketone.

Whatever the technique, all of the known processes are difficult to carry out on an industrial scale.

SUMMARY OF THE INVENTION

Accordingly, a major object of the present invention is the provision of an improved, yet simple industrial process for the α-alkylation of ketones.

Briefly, the present invention features the C-alkylation of ketones containing at least one hydrogen atom or ester group in the α-position with respect to the carbonyl group, wherein such ketones are alkylated in the α-position with respect to the carbonyl group in the presence of a catalytically effective amount of a condensed or uncondensed orthophosphate anion.

DETAILED DESCRIPTION OF BEST MODE AND PREFERRED EMBODIMENTS OF THE INVENTION

More particularly according to the present invention, by the term "ketone" is intended an acyclic or cyclic hydrocarbon containing at least one carbonyl group and having at least one hydrogen atom or ester group in the α-position with respect to such carbonyl group.

There can be more than one carbonyl group present in the starting substrate, for example two, i.e., the ketone is then a dione.

In a first embodiment of the invention, a ketone containing at least one hydrogen atom in the α-position as regards the carbonyl group is reacted with an alkylating agent.

In another embodiment of the invention, a ketone containing at least one ester group in the α-position with respect to the carbonyl group is the starting material. In this instance, the alkylating agent need not be supplied externally, but can be generated in situ from the ester group.

By the term "ester group" is intended a —$COOR_e$ radical in which $R_e$ is the alkylating radical which itself bonds in the α-position with respect to the carbonyl group. It can be of any nature and the selection thereof depends on the group sought to be introduced. Preferably, the radical $R_e$ is a linear or branched alkyl radical having from 1 to 6 carbon atoms, preferably 1 to 4 carbon atoms; $R_e$ more preferably is a methyl or ethyl radical.

The process of the present invention is applicable to any cyclic or noncyclic ketone.

It is particularly well suited for cyclic ketones in which the number of carbonyl groups in the ring is greater than 1.

Since the cyclic starting ketone employed in the process of the invention can be polycyclic, in particular bicyclic, it will be appreciated that the number of carbonyl groups in the starting ketone can equal 3 or 4, or more.

The cyclic ketone used in the process of the invention can be a mono- or polycarbonyl ketone. It can be a monocyclic or polycyclic ketone.

The process of the invention is particularly well suited for the alkylation of cyclic ketones having the following general formula (Ia):

wherein A represents the remainder or residue of a cycle or ring member which constitutes all or a part of a monocyclic or polycyclic ring system containing at least one carbonyl group and having at least one hydrogen atom or ester group in the α-position with respect to the carbonyl group; R is a hydrogen atom, or one or more substituents which may be identical or different; and n is a number which is preferably equal to 1 or 2.

Exemplary residues A, which may be substituted, include the residues of:

(i) saturated or unsaturated monocyclic or carbocyclic compounds;

(ii) polycyclic compounds comprising at least two saturated and/or unsaturated carbocycles;

(iii) polycyclic compounds comprising at least two saturated and/or unsaturated cycles, in which one or more of the carbon atoms can be replaced by a heteroatom;

(iv) polycyclic compounds comprising at least two carbocycles, one of which is aromatic.

The cyclic ketone of formula (Ia) can thus be monocyclic or polycyclic.

When the compound is monocyclic, the number of carbon atoms in the cycle or ring can vary widely from 3 to 20 carbon atoms, and preferably has 5 or 6 carbon atoms. The carbocycle can be saturated or contain 1 or 2 sites of unsaturation in the cycle, preferably 1 or 2 double bonds which are typically in the α-position vis-a-vis the carbonyl group.

The compound can also be polycyclic, preferably bicyclic, i.e., at least two ring members have two carbon atoms in common.

When the compound is polycyclic, the number of carbon atoms in each ring is lower, generally ranging from 3 to 8, preferably 5 or 6 carbon atoms.

The polycyclic compound can contain at least two saturated and/or unsaturated ring members, in which one or more (preferably two) carbon atoms can be replaced by a heteroatom, preferably an oxygen or nitrogen atom.

The polycyclic compound can contain at least two carbocycles, one of which is aromatic, the aromatic cycle preferably being a benzene ring.

The cyclic ketone of formula (Ia) may be substituted by one or more substituents.

The number of substituents on the cycle depends on the number of carbon atoms contained therein and the presence or absence of unsaturated bonds in the ring.

The maximum number of substituents which can be borne by a particular cycle is readily apparent to one skilled in this art.

With a saturated carbocycle, the maximum number of substituents equals $2\rho-3$, $\rho$ representing the number of carbon atoms in the ring. This number is reduced by two for every double bond, or where the cycles are fused.

In general, the number of substituents present on the cycle ranges from 1 to 5 and is usually 1, 2 or 3.

Representative substituents will now be more fully described. Any substituent can be present on the cycle provided that it does not interfere with the subject alkylation reaction. Exemplary substituents which can be borne by the residue A include:

(A) R can represent $R_0$, one of the following groups:

(a) a linear or branched acyclic aliphatic radical having from 1 to 20 carbon atoms, which may be saturated or contain one or more unsaturated bonds in the chain, preferably 1 to 3 unsaturated bonds which are preferably simple or conjugated double bonds; the hydrocarbon chain may be interrupted by one of the following groups represented by Z, i.e., —O—; —CO—; —COO—; —NR$_2$; —CO—NR$_2$; —S—; —SO$_2$— in which R$_2$ is a hydrogen atom, or a linear or branched alkyl radical having from 1 to 6 carbon atoms; and/or (b) one of the following substituents: —OH; —CN; —N[R$_2$]$_2$; —COOR$_2$; —CF$_3$ or —X in which the radicals R$_2$, which may be identical or different, are each a hydrogen atom or a linear or branched alkyl radical having from 1 to 6 carbon atoms and X is a halogen atom, preferably fluorine, chlorine or bromine;

(c) an =R$_3$ radical in which R$_3$ is an alkylidene radical having from 1 to 6 carbon atoms, a radical having the formula =C(CN)$_2$ or a cycloalkylidene or cycloalkenylidene radical having 5 or 6 carbon atoms, or a benzylidene radical which may be substituted, preferably by a halogen atom X;

(d) a linear or branched alkoxy radical having from 1 to 6 carbon atoms;

(e) two successive atoms of the cycle may be joined together via an epoxy bridge or by an alkylenedioxy bridge having from 1 to 4 carbon atoms, preferably methylenedioxy, ethylenedioxy or propylenedioxy radicals;

(f) an OH group;

(g) a COOR$_4$ group in which R$_4$ is a hydrogen atom or an alkyl radical having from 1 to 4 carbon atoms, preferably methyl or ethyl;

(h) a CN group;

(i) a halogen atom, preferably fluorine, chlorine or bromine;

(j) a —CF$_3$ group; or (B) R can represent R$_1$, one of the following more complex radicals:

(a') a saturated or unsaturated carbocyclic radical having from 4 to 7 carbon atoms, preferably a cyclopentyl, cyclohexyl, cyclopentene-2-yl, cyclopentene-3-yl, cyclohexene-1-yl, cyclohexene-2-yl or cyclohexene-3-yl radical;

(b') a radical having the formula:

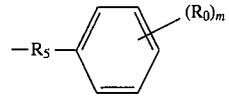

in which R$_5$ is a valence bond or a divalent, linear or branched, saturated or unsaturated divalent hydrocarbon radical having from 1 to 6 carbon atoms, for example methylene, ethylene, propylene, isopropylene or isopropylidene, R$_0$ is as defined above and m is a whole number ranging from 0 to 4;

(c') an —R$_5$—Z—R$_8$ radical in which Z and R$_5$ are as defined above, R$_8$ is a linear or branched alkyl radical having from 1 to 6 carbon atoms or a radical having the formula:

wherein R$_0$ and m are as defined above;

(d') a spiro radical having one of the formulae:

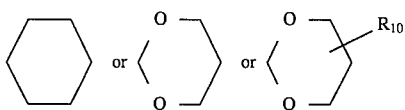

wherein R$_{10}$ is one or more linear or branched alkyl radicals having from 1 to 6 carbon atoms.

Preferably, in formula (Ia), the different variables have the following definitions:

A can be the residue or remainder of a saturated monocyclic carbocyclic compound having from 3 to 20 carbon atoms. There may be one or two carbonyl groups in the cycle. The carbonyl group is preferably borne by a saturated carbocycle having 5 or 6 carbon atoms.

The saturated carbocycle may be substituted. The number of substituents on each cycle can vary widely from 1 to 5. It is generally 1 or 2.

Specific examples of such substituents include:

(i) a linear or branched alkyl radical containing 1 to 15 carbon atoms, preferably a methyl, ethyl, n-propyl, isopropyl, n-butyl, sec-butyl, tert-butyl, n-pentyl, isopentyl, tert-pentyl, n-hexyl or n-heptyl radical;

(ii) an alkyl radical having from 1 to 15 carbon atoms substituted by a functional group, preferably an OH, CN, N[R$_2$]$_2$ or COOR$_2$ group wherein the radicals R$_2$, which may be identical or different, are each a hydrogen atom or a linear or branched alkyl radical having from 1 to 6 carbon atoms; the alkyl chain may be interrupted by an oxygen atom or a carbonyl, carboxy or amino group which itself may be substituted, in particular a radical of formula —NHCH$_3$ or —N(CH$_3$)$_2$, a radical of formula —CH$_2$—CH$_2$—CN, a radical of formula —CH$_2$—CO—(CH$_2$)$_4$—COOH, a radical of formula COCH(CH$_3$)$_2$, a radical of formula —(CH$_2$)$_6$—COOH, a radical of formula —CH$_2$—COOCH$_3$, a radical of formula —CH$_2$—COOC$_2$H$_5$, a radical of formula —CH$_2$—CH$_2$—COOCH$_3$, a radical of formula —(CH$_2$)$_6$—COOCH$_3$, a radical of formula —(CH$_2$)$_6$—COOC$_2$H$_5$, a radical of formula —(CH$_2$)$_5$—COOC$_2$H$_5$, a radical of formula C(CH$_3$)$_2$—CO—CH$_3$, a radical of formula —CH$_2$CH$_2$CO—(CH$_2$)$_4$—CH$_3$;

(iii) a linear or branched alkenylene or alkylidene radical comprising one or two double bonds and having from 1 to 15 carbon atoms, preferably a radical of formula —CH$_2$—CH=CH$_2$, a radical of formula —C(CH$_3$)=CH$_2$, a radical of formula —CH$_2$—CH=CH—(CH$_2$)$_2$—CH$_3$, a radical of formula —CH=CH—(CH$_2$)$_4$—CH$_3$, a radical of formula —CH$_2$—CH=C(CH$_3$)$_2$, or a radical of formula —CH$_2$—CH=CCH$_3$—(CH$_2$)$_2$—CH=C (CH$_3$)$_2$;

(iv) a =C (CH$_3$)$_2$ or =CH—(CH$_2$)$_2$—CH$_3$ radical;

(v) a linear or branched alkenylene or alkylidene radical comprising one or two double bonds and having from 1 to 15 carbon atoms, substituted by a functional group, preferably an OH, CN, NH$_2$ or COOR$_2$ group in which R$_2$ is as defined above: the unsaturated chain can be interrupted by an oxygen atom, a carbonyl group or a carboxy group, in particular a radical of formula —CH$_2$—CH=CH—(CH$_2$)$_3$—COOH, a radical of formula —CH=CH—C(CH$_3$)=CH—COOH, a radical of formula —CH$_2$—CH=CH—(CH$_2$)$_3$—COOCH$_3$, a radical of formula —CH=CH—C(CH$_3$)=CH—COOCH$_3$, a radical of formula —CH=CH—CO—CH$_3$, a radical of formula —CH=CH—CO—(CH$_2$)$_4$—CH$_3$ or a radical with formula —CH=CH—CHOH—(CH$_2$)$_4$—CH$_3$;

(vi) a linear or branched alkoxy radical having from 1 to 6 carbon atoms, preferably a methoxy or ethoxy radical;

(vii) two successive atoms of the cycle may be joined together via an epoxy bridge such as a methylenedioxy, ethylenedioxy or propylenedioxy radical;

(viii) a spiro type radical having one of the formulae:

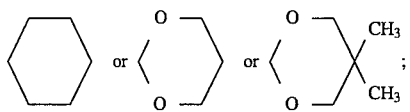

(ix) a radical having one of the formulae:

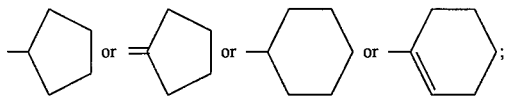

(x) a radical having one of the formulae:

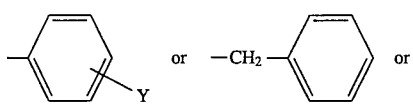

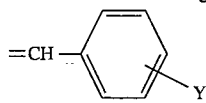

wherein Y is a hydrogen atom or a halogen atom, preferably fluorine or chlorine;

(xi) a radical having one of the formulae:

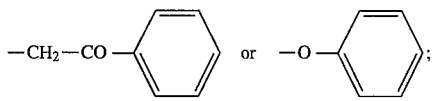

(xii) an OH group;
(xiii) a COOR$_4$ group, wherein R$_4$ is a hydrogen atom or an alkyl radical having from 1 to 4 carbon atoms, preferably methyl or ethyl;
(xiv) a CN group;
(xv) a halogen atom, preferably fluorine, chlorine or bromine.

Particularly representative compounds (Ia) have the following formulae:

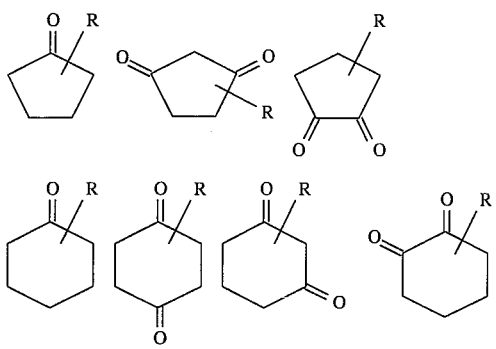

A can also be the remainder or residue of an unsaturated monocyclic carbocyclic compound having from 4 to 20 carbon atoms. The ring member may contain one or two carbonyl groups. The carbonyl group preferably comprises an unsaturated carbocycle having 5 or 6 carbon atoms.

The unsaturated carbocycle may be substituted. The number of substituents on each cycle can vary widely from 1 to 5. It is generally 1 or 2.

Specific examples of such substituents include:

(i') a linear or branched alkyl radical having from 1 to 15 carbon atoms, preferably a methyl, ethyl, n-propyl, isopropyl, n-butyl, sec-butyl, tert-butyl, n-pentyl, isopentyl, tert-pentyl, n-hexyl or n-heptyl radical;

(ii') an alkyl radical having from 1 to 15 carbon atoms and comprising a functional group, preferably an OH, CN, N[R$_2$]$_2$ or COOR$_2$ group wherein the radicals R$_2$, which may be identical or different, are each a hydrogen atom or a linear or branched alkyl radical having from 1 to 6 carbon atoms: the alkyl chain may be interrupted by an oxygen atom or a carbonyl, carboxy or amino group which itself may be substituted, in particular a radical of formula —NHCH$_3$ or —N(CH$_3$)$_2$, a radical of formula —CH$_2$—CH$_2$—CN, a radical of formula —CH$_2$—CO—(CH$_2$)$_4$—COOH, a radical of formula COCH(CH$_3$)$_2$, a radical of formula —(CH$_2$)$_6$—COOH, a radical of formula —CH$_2$—COOCH$_3$, a radical of formula —CH$_2$—COOC$_2$H$_5$ a radical of formula —CH$_2$—CH$_2$COOCH$_3$, a radical of formula —(CH$_2$)$_6$—COOCH$_3$, a radical of formula —(CH$_2$)$_6$—COOC$_2$H$_5$, a radical of formula —(CH$_2$)$_5$—COOC$_2$H$_5$, a radical of formula —CO—CH$_3$, a radical of formula —C(CH$_3$)$_2$—CO—CH$_3$, or a radical of formula —CH$_2$—CH$_2$—CO—(CH$_2$)$_4$—CH$_3$;

(iii') a linear or branched alkenylene or alkylidene radical comprising one or two double bonds and having from 1 to 15 carbon atoms, preferably a radical of formula —CH$_2$CH=CH$_2$, a radical of formula —C(CH$_3$)=CH$_2$, a radical of formula —CH$_2$—CH=CH—C$_2$H$_5$, a radical of formula CH$_2$—CH=CH—(CH$_2$)$_2$—CH$_3$, a radical of formula —CH=CH—(CH$_2$)$_4$—CH$_3$, a radical of formula —CH$_2$—CH=C(CH$_3$)$_2$, or a radical of formula —CH$_2$—CH=CCH$_3$—(CH$_2$)$_2$—CH=C(CH$_3$)2.

(iv') a =C(CH$_3$)$_2$ or =CH—(CH$_2$)$_2$—CH$_3$ radical;

(v') a linear or branched alkenylene or alkylidene radical comprising one or two double bonds and having from 1 to 15 carbon atoms, substituted by a functional group, preferably an OH, CN, NH$_2$ or COOR$_2$ group wherein R$_2$ is as defined above: the unsaturated chain can be interrupted by an oxygen atom, a carbonyl group or a carboxy group, in particular a radical of formula —CH$_2$—CH=CH—(CH$_2$)$_3$—COOH, a radical of formula —CH=CH—C(CH$_3$)=CH—COOH, a radical of formula —CH$_2$—CH=CH—(CH$_2$)$_3$—COOCH$_3$, a radical of formula —CH=CH—C(CH$_3$)=CH—COOCH$_3$, a radical of formula CH=CH—CO—CH$_3$, a radical of formula —CH=CH—CO—(CH$_2$)$_4$—CH$_3$ or a radical of formula —CH=CH—CHOH—(CH$_2$)$_4$—CH$_3$;

(vi') a linear or branched alkoxy radical having from 1 to 6 carbon atoms, preferably a methoxy or ethoxy radical;

(vii') a radical of formula:

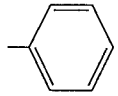

(viii') an OH group;

(ix') a COOR group, wherein R is a hydrogen atom or an alkyl radical having from 1 to 4 carbon atoms, preferably methyl or ethyl;

(x') a halogen atom, preferably fluorine, chlorine or bromine.

Particularly representative of the immediately above compounds are those having the following formulae:

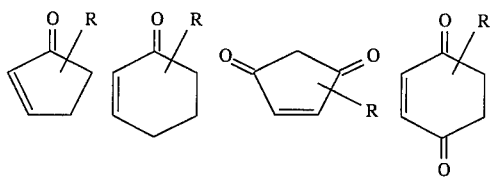

A can also represent the remainder or residue of a saturated polycyclic carbocyclic compound, preferably a bicyclic compound comprising two saturated carbocycles, each preferably having from 4 to 8 carbon atoms. One or both cycles may contain a carbonyl group. The same cycle may comprise two carbonyl groups. The carbonyl group preferably comprises one or two saturated carbocycles having 5 or 6 carbon atoms.

In the polycyclic compounds, one or more carbon atoms, preferably two, can be replaced by a heteroatom, preferably a nitrogen or oxygen atom.

The cycle(s) of the polycyclic compound may be substituted. The number of substituents on each cycle is generally 1 to 4, preferably 1 or 2. Specific examples of such substituents include:

(i") a linear or branched alkyl radical having from 1 to 6 carbon atoms, preferably a methyl or isopropyl radical;

(ii") a radical of formula —CH$_2$Br;

(iii") a linear or branched alkoxy radical having from 1 to 6 carbon atoms, preferably a methoxy radical;

(iv") a radical of formula =CH$_2$;

(v") an OH group;

(vi") a COOH group;

(vii") a halogen atom, preferably fluorine, chlorine or bromine;

(viii") a CF$_3$ group.

Particularly representative of the immediately above compounds are those having the following formulae:

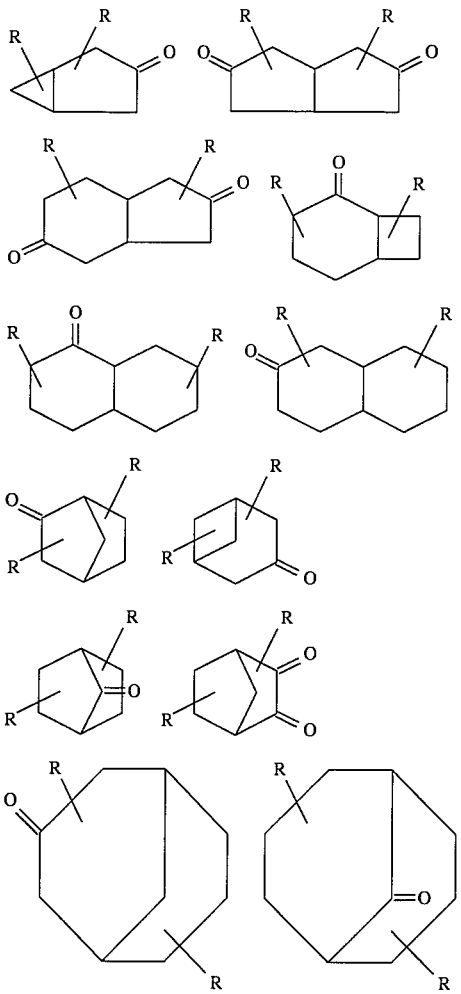

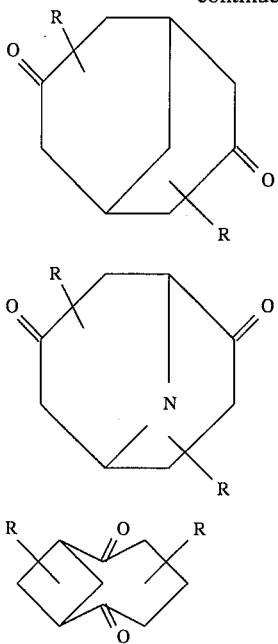

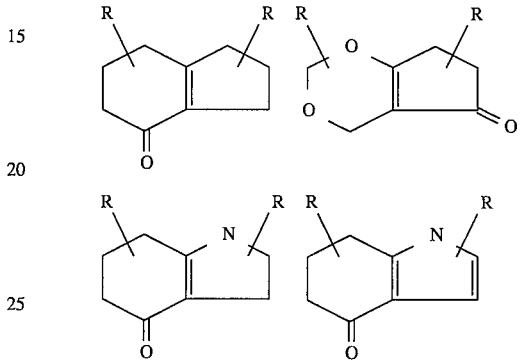

erably having 5 or 6 carbon atoms. One of the two cycles may contain a carbonyl group.

In such polycyclic compounds, one or more carbon atoms, preferably two, can be replaced by a heteroatom, preferably a nitrogen or oxygen atom.

The cycle(s) or ring member(s) of the polycyclic compound may be substituted. The number of substituents on each cycle generally ranges from 1 to 5, preferably 1 or 2.

The substituents are typically one or more linear or branched alkyl radicals having from 1 to 6 carbon atoms, preferably a methyl or ethyl radical.

Particularly representative of the immediately above compounds are those having the following formulae:

A can also represent the remainder or residue of a bicyclic carbocyclic compound comprising two carbocycles, each preferably having from 4 to 7 carbon atoms, one saturated and the other unsaturated, generally comprising a single double bond. The carbonyl group may be present in the saturated cycle or the unsaturated cycle, or in both. The carbonyl group preferably comprises a saturated or unsaturated carbocycle having 5 or 6 carbon atoms.

The cycle(s) or ring member(s) of the polycyclic compound may be substituted. The number of substituents borne by each cycle generally ranges from 1 to 3, preferably 1 or 2.

Specific examples of such substituents include:

(i''') a linear or branched alkyl radical having from 1 to 6 carbon atoms, preferably a methyl radical;

(ii''') a radical of formula

(iii''') a radical of formula —CH$_2$—O—CH$_3$;

(iv''') a halogen atom, preferably chlorine.

Particularly representative of the immediately above compounds are those having the following formulae:

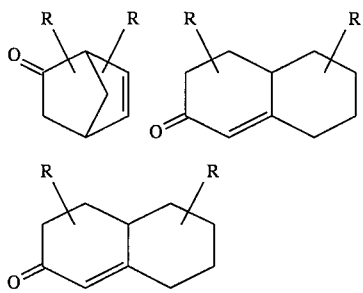

A can also represent the remainder or residue of a polycyclic carbocyclic compound, preferably a bicyclic compound comprising two unsaturated carbocycles, each pref- A too can represent the remainder or residue of a polycyclic carbocyclic compound containing at least one aromatic carbocycle, preferably a benzene ring, and a carbocycle which preferably has from 4 to 7 carbon atoms and contains one or two carbonyl groups.

A is preferably the residue or remainder of a bicyclic compound containing a benzene ring and a carbocycle having 5 or 6 carbon atoms containing one or two carbonyl groups.

The two ring members of the bicyclic radical may be substituted. The number of substituents on each ring is generally 1 or 2.

Specific examples of such substituents are:

(i'''') a linear or branched alkyl radical having from 1 to 6 carbon atoms, preferably a methyl or tert-butyl radical;

(ii'''') a radical of formula

(iii'''') a linear or branched alkoxy radical having from 1 to 6 carbon atoms, preferably a methoxy radical;

(iv'''') a linear or branched alkoxy radical having from 1 to 6 carbon atoms bearing other functional groups such as an OH and/or N[R$_2$]$_2$ group wherein the radicals R$_2$, which may be identical or different, are each a hydrogen atom or a linear or branched alkyl radical having from 1 to 6 carbon atoms, preferably a radical of formula —O—CH$_2$—CHOH—CH$_2$—NHBu-t;

(v'''') an OH group;

(vi'''') an acyl group having from 2 to 6 carbon atoms, preferably an acetyl radical or a radical of formula —CO-tert-butyl;

(vii'''') a —CH$_2$—COOH group;

(viii'''') an —NH$_2$ group;

(ix'''') a halogen atom, preferably fluorine, chlorine or bromine.

Particularly representative of the immediately above compounds are those having the following formulae:

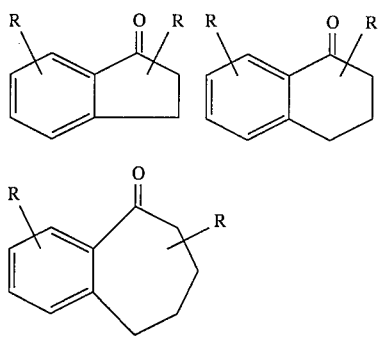

Among the cyclic ketones indicated above, the process of the invention is particularly applicable to carbocyclic ketones containing at least one hydrogen atom or a saturated or unsaturated ester group in the α-position with respect to the carbonyl group, containing 5 to 6 carbon atoms in the ring, and having formula (Ia) wherein R is a hydrogen atom, a linear or branched alkyl or alkoxy radical having from 1 to 6 carbon atoms, preferably 1 to 4 carbon atoms, or a benzylidene radical which may be substituted by a halogen atom, and n equals 1.

Cyclic ketones having formula (Ia) and which are preferably employed in the process of the invention include:

(1) Those in which A is the residue of a saturated monocyclic compound containing a single carbonyl group, such as:
Cyclobutanone,
Cyclopentanone,
2-Methylcyclopentanone,
3-Methylcyclopentanone,
2-Methyl-2-carboxymethylcyclopentanone,
2,2-Dimethylcyclopentanone,
2-(2-Octenyl)-cyclopentanone,
2-(3,7-Dimethyl-2,6-octadienyl)cyclopentanone,
2- Cyclopentylidenecyclopentanone,
2-Benzylidenecyclopentanone,
2-[(p-Chloro)benzylidenelcyclopentanone,
2-Methyl-2-carboxymethyl-5-[(p-chloro)benzylidene cyclopentanone,
2,4-Dimethylcyclopentanone,
2,5-Dimethylcyclopentanone,
3,4-Dimethylcyclopentanone,
2,2,4-Trimethylcyclopentanone,
5-Methyl-2-(1-methylethylidene)cyclohexanone,
6-Ketoprostaglandin E1,
Methylester prostaglandin E2,
Prostaglandin D2,
Cyclohexanone,
3-Methylcyclohexanone,
4-n-Pentylcyclohexanone,
2-(N,N-Dimethylamino)cyclohexanone,
3,5-Dimethylcyclohexanone,
Dihydrocarvone,
Cycloheptanone,
Cyclooctanone,
Cycloheptadecanone;

(2) Those in which A is the residue of a saturated monocyclic compound containing two carbonyl groups, such as:
1,3-Cyclopentanedione,
2-Allyl-2-methyl-1,3-cyclopentanedione,
3,3-Dimethyl-1,2-cyclopentanedione,
3,4-Dimethyl-1,2-cyclopentanedione,
1,2-Cyclohexanedione,
1,3-Cyclohexanedione,
1,4-Cyclohexanedione,
1,2-Cycloheptanedione;

(3) Those in which A is the residue of an unsaturated monocyclic compound containing a single carbonyl group, such as:
2-Cyclopentenone,
3-Methyl-2-cyclopentenone,
4,4-Dimethyl-2-cyclopentenone,
2-Pentyl-2-cyclopentenone,
3-Ethoxy-2-cyclopentenone,
2-Hydroxy-3-ethyl-2-cyclopentenone,
Prostaglandin J2,
Jasmone,
2-Hydroxy-3,4-dimethyl-2-cyclopentenone,
15-Oxoprostaglandin E2,
2-Ethoxy-2-cyclohexenone,
3-Bromo-2-cyclohexenone,
Carvone,
8-Hydroxycarvotanacetone,
2-Methyl-5-(1-methylethenyl)-2-cyclohexenone,
3,5,5-Trimethyl-2-cyclohexenone,
Methyl ester of abscisic acid,
2-Hydroxy-3-methyl-6-(1-methylethyl)-2-cyclohexenone,
5-Cyclohexadecenone;

(4) Those in which A is the residue of an unsaturated monocyclic compound containing two carbonyl groups, such as:
2-Cyclopentene-1,4-dione,
4-Hydroxy-5-methyl-4-cyclopentene-1,3-dione;

(5) Those in which A is the residue of a saturated bicyclic compound containing one or two carbonyl groups, such as:
Camphor,
Norcamphor,
3-Bromocamphor,
2,3-Bornanedione,
1-Decalone,
2-Decalone,
N-(Ethoxycarbonyl)nortropinone;

(6) Those in which A is the residue of a saturated/ unsaturated bicyclic compound containing one or two carbonyl groups, such as:
Bicyclo[3.2.0]hept-2-en-6-one,
1-(Methoxymethyl)-bicyclo[2.2.0]hept-5-en-2-one,
3,4,8,8a-Tetrahydro-8a-methyl-1,6(2H, 7H)-naphthalenedione;

(7) Those in which A is the residue of an unsaturated bicyclic compound containing one carbonyl group, such as:
6,7-Dihydro-cyclopenta-1,3-dioxin-5(4H)-one,
6,7-Dihydro-1,1,2,3,3-pentamethyl-4(5H)-indanone,
4-Oxo-4,5,6,7-tetrahydroindole;

(8) Those in which A is the residue of a bicyclic compound in which one ring is aromatic and contains one or two carbonyl groups, such as:
2-Indanone,
2-Methyl-1-indanone,
4-Methyl-1-indanone,
4-Methoxy-1-indanone,
6-Methoxy-1-indanone,
4-Hydroxy-1-indanone, 5-Bromo-1-indanone,
1,3-Indanedione,
1-Tetralone,
2-Tetralone,
4-Methyl-1-tetralone,
5,7-Dimethyl-1-tetralone,
5-Methoxy-1-tetralone,
6,7-Dimethoxy-1-tetralone,
5-Hydroxy-1-tetralone,
Levobunolol.

When the starting compound is an acyclic ketone, exemplary are those having the following general formula (1b):

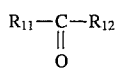

$$R_{11}-\underset{\underset{O}{\|}}{C}-R_{12} \quad (1b)$$

in which $R_{11}$ and $R_{12}$, which may be identical or different, are each a hydrocarbon radical having from 1 to 20 carbon atoms which can be a linear or branched, saturated or unsaturated aliphatic acyclic radical; a saturated or unsaturated, monocyclic or polycyclic, aromatic carbocyclic or heterocyclic radical; a linear or branched, saturated or unsaturated aliphatic radical substituted by a cyclic substituent, with the proviso that at least one of the radicals $R_{11}$ and $R_{12}$ contains a carbon atom in the α-position with respect to the carbonyl group which is substituted by at least one hydrogen atom or ester group.

In general ketone formula (1b), $R_{11}$ and $R_{12}$, which may be identical or different, are, advantageously, each a linear or branched, saturated or unsaturated acyclic aliphatic radical.

Especially, $R_{11}$ and $R_{12}$ are each a linear or branched acyclic aliphatic radical preferably having from 1 to 12 carbon atoms, which may be saturated or contain one or more unsaturated bonds in the chain, generally 1 to 3 unsaturated bonds which can be simple or conjugated double bonds; the hydrocarbon chain may be interrupted by a group such as the Z groups defined above and/or bear one of the following substituents as defined above: —OH; —CN; —N[$R_2$]$_2$; —COOR$_2$; —CF$_3$ or —X.

The linear or branched, saturated or unsaturated acyclic aliphatic residue may be substituted by a cyclic substituent. By the term "cycle" is intended a saturated, unsaturated or aromatic carbocyclic or heterocyclic ring member.

The acyclic aliphatic residue can be bonded to the cycle via a simple valence bond or by one of the Z groups.

Exemplary cyclic substituents include aromatic or heterocyclic cycloaliphatic substituents, in particular cycloaliphatic radicals having 6 carbon atoms in the ring, or benzene rings, and such cyclic substituents can themselves be substituted.

In general formula (1b) for acyclic ketones, one of radicals $R_{11}$ or $R_{12}$ may also be a saturated or unsaturated cyclic hydrocarbon radical preferably having 5 or 6 carbon atoms in the ring; a saturated or unsaturated heterocyclic radical, having, in particular, 5 or 6 atoms in the ring, 1 or 2 of which are heteroatoms such as nitrogen, sulfur or oxygen atoms; or an aromatic, monocyclic or polycyclic hydrocarbon which may or may not be condensed.

Exemplary of these latter ketones which are well suited for the process of the invention are:

(a) Saturated aliphatic ketones:
   Acetone,
   Methylethylketone,
   Methylisopropylketone,
   Methylisobutylketone,
   2-Pentanone,
   3-Pentanone,
   2-Carboxymethyl-3-pentanone,
   2-Hexanone
   3-Hexanone,
   5-Methyl-2-hexanone,
   2-Heptanone,
   3-Heptanone,
   4-Heptanone,
   2-Octanone,
   3-Octanone,
   Diisobutylketone,
   5-Methyl-2-octanone,
   2-Nonanone,
   2,6,8-Trimethyl-4-nonanone;

(b) Ketones substituted by a functional group:
   1,3-Dihydroxy-2-propanone,
   Diacetone alcohol,
   Triacetone alcohol,
   4-Methoxy-4-methyl-2-pentanone;

Unsaturated aliphatic ketones:
   Mesityl oxide,
   3-Butene-2-one,
   4-Methyl 4-pentene-2-one;

(d) Aliphatic diketones:
   2,3-Pentanedione,
   2,3-Hexanedione,
   3,4-Hexanedione,
   4-Methyl-2,3-pentanedione,
   3,4-Heptanedione,
   5-Methyl-2,3-hexanedione,
   2,3-Octanedione,
   4,5-Octanedione,
   2,5-Dimethyl -3,4-hexanedione,
   5-Methyl-3,4 -heptanedione,
   6-Methyl-3,4 -heptanedione,
   1-Phenyl-1,2-propanedione,
   2,4-Pentanedione,
   2,4-Hexanedione,
   2,4-Heptanedione,
   1-Phenyl-1,3-butanedione,
   1-Phenyl-1,3-pentanedione,
   1,3-Diphenyl-1,3-propanedione,
   1-Phenyl-2,4-pentanedione,
   2,5-Hexanedione,
   3,4-Dimethyl-2,5-hexanedione,
   3,3,4,4-Tetramethyl-2,5-hexanedione,
   2,5-Heptanedione,
   3,6-Octanedione,
   6-Methyl-2,5-heptanedione,
   2,5-Decanedione,
   2,5-Dodecanedione,
   1,4-Diphenyl-1,4-butanedione;

(e) Mixed aliphatic and carbo- or heterocyclic ketones:
   Acetophenone,
   Propiophenone,
   2,2-Diethoxyacetophenone,
   Acetylpyrazine,
   2-Acetylpyridine,
   3-Acetylpyridine,
   4-Acetylpyridine,
   2-Acetylpyrrole,
   2-Acetyl-1-tetralone.

In the process of the invention, the C-alkylation reaction of the ketone is carried out using an alkylating agent in the presence of a catalyst.

A variety of alkylating agents are suitable for carrying out the process of the invention. Thus, an organic ester can be used, more particularly an organic ester having the following general formula (II):

$$[R_a\text{—CO—O}]_p R_b \quad \text{(II)}$$

wherein $R_a$ is a radical $R_c$, advantageously a hydrocarbon radical having from 1 to 12 carbon atoms and which may be a linear or branched, saturated or unsaturated aliphatic radical which may be substituted by a halogen atom, preferably a chlorine atom; a monocyclic or polycyclic, saturated or unsaturated carbocyclic radical; or a linear or branched, saturated or unsaturated acyclic aliphatic radical bearing a cyclic substituent; an $R_d$—O—CO—$R_f$ radical in which $R_d$ has the definition of the radical $R_c$ and $R_f$ is a simple valence bond or a linear or branched, saturated or unsaturated divalent aliphatic radical containing at least one carbon atom; a $R_d$—O— radical in which $R_d$ has the definition of radical $R_c$; or a $R_d$—O—CO—O— radical in which $R_d$ has the definition of $R_c$; $R_b$ is an $R_c$ radical as defined above, or an alkali or alkaline earth metal, with the proviso that $R_a$ and $R_b$ can together form a linear or branched, saturated or unsaturated divalent aliphatic radical having at least 2 carbon atoms, and p is a whole number equal to 1 or 2.

The general formula (II) also includes carboxylic acid esters and organic carbonates, or mixed organometallic carbonates.

Particularly exemplary compounds of general formula (II) include the carboxylic acid esters having formula (IIa):

$$R_a\text{—CO—O—}R_b \quad \text{(IIa)}$$

wherein $R_a$ is a linear or branched alkyl radical having from 1 to 6 carbon atoms, preferably 1 to 3 carbon atoms; a cycloalkyl radical having 5 or 6 carbon atoms, preferably 6 carbon atoms; an aralkyl radical having from 7 to 12 carbon atoms; an $R_c$—O—CO—$R_d$ radical in which $R_c$ has the definition of $R_a$ and $R_d$ is a valence bond or an alkylene radical having from 1 to 6 carbon atoms; and $R_b$ is a linear or branched alkyl radical having from 1 to 6 carbon atoms, or a cycloalkyl radical having 5 or 6 carbon atoms, with the proviso that $R_a$ and $R_b$ may together form an alkylene radical having from 2 to 4 carbon atoms.

The organic esters which are the preferred are those of formula (IIa) wherein $R_a$ is a linear or branched alkyl radical having from 1 to 6 carbon atoms, preferably 1 to 4 carbon atoms, and $R_b$ is a linear or branched alkyl radical having from 1 to 4 carbon atoms.

Exemplary carboxylic acid esters of formula (IIa) include alkyl esters, preferably methyl or ethyl esters, of saturated aliphatic monocarboxylic acids such as acetic, propionic, butyric, isobutyric, valeric, isovaleric or pivalic acid, and saturated aliphatic dicarboxylic acids such as oxalic acid, succinic acid, glutaric acid or adipic acid.

For the sake of economy, the preferred esters from among the above are methyl acetate and ethyl acetate.

organic carbonates and mixed organometallic carbonates are also suited for carrying out the process of the invention.

Representative organic carbonates and mixed organometallic carbonates suitable for use according to the invention are those having the following general formula (IIb):

$$[R_a\text{—O—CO—O}]_p R_b \quad \text{(IIb)}$$

wherein $R_a$ is a linear or branched alkyl radical having from 1 to 6 carbon atoms, which may be substituted by a halogen atom, preferably a chlorine atom, a cycloalkyl radical having 5 or 6 carbon atoms, an aryl radical having from 6 to 12 carbon atoms, an $R_d$—O—CO—$R_d$ radical in which $R_d$ is a linear or branched alkyl radical having from 1 to 6 carbon atoms or a cycloalkyl radical having 5 or 6 carbon atoms; $R_b$ is a linear or branched alkyl radical having from 1 to 6 carbon atoms, a cycloalkyl radical having 5 or 6 carbon atoms, or an alkali or alkaline earth metal, preferably sodium or potassium; and p=1, or p=2 when $R_b$ is an alkaline earth metal; with the proviso that $R_a$ and $R_b$ may together form an alkylene radical having from 2 to 6 carbon atoms.

The organic carbonates which are the preferred are those of formula (IIb) wherein $R_a$ and $R_b$, which may be identical or different, are each a linear or branched alkyl radical having from 1 to 6 carbon atoms, preferably 1 to 4 carbon atoms.

Exemplary organic or organometallic carbonates include ditertiobutyl carbonate, diethyl carbonate, dimethyl carbonate, ethylene carbonate, propylene carbonate, phenyl tertiobutyl carbonate, sodium tertiobutyl carbonate, ditertiobutyl dicarbonate, and chloromethyl methyl carbonate.

Dialkylsulfates may also be employed as alkylating agents, more particularly dialkylsulfates having the formula $R_g$—O—$SO_2$—O—$R_h$, in which $R_g$ and $R_h$, which may be identical or different, are each a linear or branched alkyl radical having from 1 to 6 carbon atoms.

Dimethylsulfate is the preferred such alkylating agent.

An alcohol may also be employed as the alkylating agent, preferably an alcohol having the formula (IIc):

$$R_i\text{—OH} \quad \text{(IIc)}$$

wherein $R_i$ is a hydrocarbon radical having from 1 to 12 carbon atoms, which may be a linear or branched, saturated or unsaturated acyclic aliphatic radical, a saturated or unsaturated, monocyclic or polycyclic cycloaliphatic radical, or a linear or branched, saturated or unsaturated aliphatic radical substituted by a cyclic substituent.

The preferred alcohols of formula (IIc) are lower alcohols in which $R_i$ is a linear or branched alkyl radical having from 1 to 6 carbon atoms, preferably 1 to 4 carbon atoms.

Methanol or ethanol are particularly preferred.

The C- or α-alkylation of the ketone in the process of the invention is carried out in the presence of a catalyst comprising a condensed or uncondensed orthophosphate anion.

The orthophosphate can be employed in the process of the invention in any form. However, for reasons of economy, it is preferable to use the readily available commercial forms.

There are three categories of orthophosphates, namely, dihydrogen phosphates, monohydrogen phosphates and phosphates.

The orthophosphates are the preferred, but condensed phosphates can also be used, i.e., phosphates containing more than one phosphorus atom. These are formed by linking tetrahedral $PO_4$ structural units together via oxygen atoms. These units can, for example, form linear polyphosphate chains having from 2 to 10 phosphorus atoms. Specific examples thereof are anions respectively having 2 or 3 phosphorus atoms, such as pyrophosphate $P_4O_7^{2-}$ or tripolyphosphate $P_3O_{10}^{5-}$.

The counter-ion can be of any type. It can be a metallic element, more particularly an element of Group 1a, 2a or 3b of the Periodic Table, or an ammonium cation.

The Periodic Table is published, for example, in the *Bulletin de la Société Chimique de France*, No.1 (1966).

The catalyst is preferably a metallic or ammonium orthophosphate. Mixtures, or mixtures of the salts thereof, may also be employed.

Exemplary phosphates well suited for carrying out the process of the invention include:

Sodium orthophosphate,
Potassium orthophosphate,
Aluminum orthophosphate,
Ammonium orthophosphate,
Silver orthophosphate,
Barium orthophosphate,
Calcium orthophosphate,
Chromium orthophosphate,
Cobalt orthophosphate,
Copper orthophosphate,
Magnesium ammonium orthophosphate,
Iron orthophosphate,
Lithium orthophosphate,
Magnesium orthophosphate,
Manganese orthophosphate,
Potassium orthophosphate,
Zinc orthophosphate,
Sodium monohydrogen phosphate,
Calcium monohydrogen phosphate,
Magnesium monohydrogen phosphate,
Zirconium monohydrogen phosphate,
Sodium pyrophosphate,
Potassium pyrophosphate,
Calcium pyrophosphate,
Copper pyrophosphate,
Zinc pyrophosphate,
Sodium pentapolyphosphate $Na_7P_5O_{16}$,
Sodium tripolyphosphate $Na_5P_3O_{10}$,
Potassium tripolyphosphate $K_5P_3O_{10}$.

The phosphate can be used in the anhydrous or hydrated state.

The preferred catalysts are sodium or potassium orthophosphates, pyrophosphates, tripolyphosphates or pentapolyphosphates.

In a preferred embodiment of the invention, a Group 3a metal orthophosphate is used, i.e., an orthophosphate of a trivalent rare earth represented by formula (III):

$$MPO_4 \qquad\qquad (III)$$

wherein M is a trivalent rare earth, i.e., a lanthanide having an atomic number of 57 to 71, yttrium or scandium.

Among the suitable catalysts, a first group of light rare earth orthophosphates, also designated the ceric rare earths, including the elements La, Ce, Pr, Nd, Sm and Eu, are preferred. These orthophosphates are dimorphic. They have a hexagonal crystalline structure and evolve towards a monoclinic structure when heated to a temperature of 600° C.–800° C.

A second suitable group of rare earth orthophosphates includes the orthophosphates of Gd, Tb and Dy. These have the same structure as that of the ceric rare earth orthophosphates but have an additional third crystalline phase with a quadratic structure at high temperatures (about 1,700° C.).

A third rare earth orthophosphate family includes the orthophosphates of heavy rare earths, also known as the yttric rare earths, including Y, Ho, Er, Tm, Yb and Lu. These compounds crystallize only in the quadratic form.

The light rare earth orthophosphates constitute the preferred rare earth orthophosphate class.

The preferred catalysts of the invention of formula (III) are those wherein M is lanthanum, cerium or samarium.

Any oxygen-containing phosphorous compound which, during synthesis of the catalyst or during the reaction, produces a rare earth orthophosphate, is also within the scope of this invention.

The starting rare earth metal orthophosphates employed in the process of the invention are known compounds. Commercially available phosphates can be used, in particular lanthanum orthophosphate, or they may be synthesized via techniques described in the literature.

The general techniques for the production of phosphates (in particular P. Pascal, *Nouveau traité chimie minérale*, volume X, pp. 821–823 (1956) and *Gmelins Handbuch der anorganischen Chemie* (8th edition), vol. 16 (0), pp. 202–206 (1965)), are of two basic categories: first, precipitation of a soluble metal salt (chloride, nitrate) using ammonium hydrogen phosphate or phosphoric acid; second, reacting a metal oxide with hot phosphoric acid. In both instances, a final treatment with an alkaline hydroxide is carried out.

Orthophosphates of said metals can also be prepared by solid/solid reaction of the salts thereof with phosphorous salts, followed by calcination.

Particular references for the preparation of particular compounds include:

Cerium orthophosphate; Fukuo et al, *Nippon Kagakkai Shi* (Reviews of the Japanese Institute of Chemistry), 4, pp. 622–626 (1975);

Lanthanum orthophosphate, J. M. Cowley et al, *Journal of Catalysis*, 56, pp. 185–194 (1979);

Yttrium orthophosphate, L. S. Eshchenko et al, *Russian Journal of Inorganic Chemistry*, 30, (6), (1985).

The product is then dried using known techniques. This is advantageously carried out at a temperature ranging from 50° C. to 200° C., for a period of time preferably of 2 to 8 hours, in a normal atmosphere or under reduced pressure (for example 10 mm of mercury=1,300 Pa), or by freeze drying.

The dried material can then be calcined at a temperature of from 200° C. to 1,000° C., preferably from 400° C. to 800° C. for a period of time of 1 to 15 hours, preferably 3 to 6 hours.

In another embodiment of the process of the invention, a trivalent rare earth orthophosphate is used doped with an alkali metal or an alkaline earth metal.

By the term "doping agent" or "dopant" is intended the alkali or alkaline earth element.

Thus, the catalyst of the invention advantageously has the following formula (IIIa):

$$MPO_4(Im)_p \qquad\qquad (IIIa)$$

wherein M is a trivalent rare earth $M_3$ or a mixture of at least one trivalent rare earth $M_3$ and at least one element selected from among the alkali metals $M_1$ and alkaline earth metals $M_2$ in the relationship:

$$M=\alpha M_1^+ + \beta M_2^{++} + \gamma M_3^{3+} \text{ and } \alpha + 2\beta + 3\gamma = 3;$$

Im represents a basic impregnating compound comprising an alkaline earth metal, preferably an alkali metal, and mixtures thereof, associated with a counter-anion to provide electrical neutrality; $\alpha$ is a coefficient ranging from 0 to 3, advantageously greater than 0.01 and equal to 0.5 at most, preferably ranging from 0.05 to 0.2; $\beta$ is a coefficient ranging from 0 to 3/2, preferably ranging from 0 to 1/3, or 1±0.1; $\gamma$ is a coefficient ranging from 0 to 1, advantageously at least equal to 1/3, preferably 1/2; and p is less than 0.5, advantageously between 0.04 and 0.25.

In formula (IIIa), $M_1$ is preferably selected from among the Group 1a elements and mixtures thereof preferably alkali metals such as lithium, sodium, potassium, rubidium, cesium and francium; $M_2$ is preferably selected from among the Group 2a elements mixtures thereof, preferably alkaline earth metals such as beryllium, magnesium, calcium, strontium, barium and radium; and $M_3$ is preferably selected from among the trivalent rare earths such as the lanthanides, yttrium and scandium and mixtures thereof, preferably lanthanides such as lanthanum, cerium, praseodymium, neodymium, samarium, europium, gadolinium, terbium, dysprosium, holmium, erbium, thulium, ytterbium and lutetium.

Typically, and for the sake of convenience, M is at most three elements; for the same reasons, it is economically advantageous to employ commercially available rare earth mixtures as such, provided they readily form the catalyst of the invention. Thus, as long as it is not critical, γ is close to one (0.9±0.1) and M is a single metal with only its impurities.

Im is an impregnating compound comprising an alkali or alkaline earth metal, preferably an alkali metal, and mixtures thereof, associated with one or more counter-anions to provide electrical neutrality.

Im is advantageously different than $MPO_4$, particularly when the impregnating agent is an alkaline earth metal.

The original counter-anion(s), i.e., prior to heat treatment, are preferably selected from among nitrate, sulfate, chloride, fluoride, hydrogen phosphate, phosphate, hydrogen sulfate, sulfate anions, and the like.

The anions can be a single species, or a mixture of species; for reasons of simplicity, it is preferably a single species or a single group of species.

The amount of doping agent in the catalyst is generally such that the percentage by weight of doping agent, with respect to the trivalent rare earth phosphate, ranges from 0% to 25%, preferably from 3% to 15%.

The catalysts employed in the process of the invention are known materials and are described in European patent application EP-A-0,440,555. Processes for the preparation thereof are also described in said European patent application EP-A-0,440,555 hereby expressly incorporated by reference.

The technique for the production of said compounds entails impregnating a compound of formula $MPO_4$, with M being defined as above, with an impregnating solution Imp, also as defined above, in a volatile solvent, preferably water.

The $MPO_4$ can be chemically modified by dry or wet impregnation.

One preparatory technique entails dry impregnating a metallic orthophosphate $MPO_4$ using a solution of at least one alkali metal or alkaline earth metal. As indicated above, preferred anions are the hydrogen phosphate or the phosphate, preferably cesium hydrogen phosphate.

Dry impregnation is carried out, i.e., the total volume of solution employed is approximately equal to the total pore volume in the trivalent rare earth metal orthophosphate. The product obtained is dried and calcined.

More especially, dry impregnation entails adding a volume V of an aqueous solution of one or more salts of cations or anions, for fixing onto the solid surface, to a mass $m_1$ of powdered product for impregnation. The volume V of solution is selected such that $V/m_1$ equals the pore volume in water of the solids for impregnation.

The concentration C of cations or anions in the impregnating solution is selected such that the ratio $CVM_2/m_1$ is equal to the percentage by weight of the impregnating species fixed on the surface of the product for impregnation ($M_2$=molar weight of impregnating species). The solution is added dropwise to ensure homogeneous adsorption.

The product can then be maintained for a period of time at room temperature. The product is then dried using conventional techniques known to this art. Drying is generally carried out at atmospheric pressure, under reduced pressure, or by freeze drying. It can also be calcined.

Wet impregnation is effected by dispersing a trivalent rare earth metal orthophosphate in an aqueous solution of cation and/or anion salts for fixing on the solid surface.

This solution can be at a concentration of $10^{-}M$ to 10M of impregnating species.

The pH of the solution is advantageously adjusted to a value at least equal to the isoelectric point of the product for modification, to preferentially fix the cations (normal case); however, this is not mandatory. The cations can be fixed below the isoelectric point when the associated anions are very "covalent" in character, such as sulfates and phosphates.

The solution temperature can range from room temperature to 100° C.

The dispersion is vigorously stirred for a period of time.

The product is then filtered and may be washed.

In these two embodiments for the preparation of these chemical compounds, it should be noted that drying is advantageously carried out at a temperature ranging from 50° C. to 200° C. for a period of time which preferably ranges from 2 to 8 hours.

Calcining is carried out at a temperature of from 200°C. to 1,000° C., preferably from 400° C. to 800° C., for a period of time of from 1 to 15 hours, preferably 3 to 6 hours.

The preferred catalysts of the invention have formula (III) in which M is lanthanum, cerium or samarium which may be doped with an alkali metal, preferably cesium.

The catalysts are those in which the surface of the catalytic article is formed at least in part by a compound in accordance with the present invention.

The catalytic phase can be used pure or supported. By the term "catalytic article" is intended the catalyst in its particular unitary form, whether or not the catalyst is supported. The catalytic phase is deposited onto the support using techniques which are well known to this art.

The catalytic articles may be in any form known for solid catalysts suitable for gaseous phase reactions.

The remainder of the catalytic article, i.e., the portion thereof which does not come into contact with the gaseous reaction mixture, can be of any material, provided that it is inert under the operating conditions; for ease of manufacture, it can be produced from compounds selected from among the phosphates, mono- and dihydrogen phosphates, and mixtures thereof. The catalysts can also be completely composed of chemical compounds (III) or (IIIA) of the present invention.

The catalyst can be in a number of different forms: powder, or shaped materials such as granules (cylinders, for example), spheres, beads, pellets or monoliths (honeycombs) produced by extrusion, molding, compression, or any other known technique.

The specific surface area of the catalyst is as high as possible, generally at least 1 $m^2$, advantageously at least 10 $m^2$, more typically ranging from 50 to 150 $m^2/g$, preferably from 50 to 100 $m^2/g$.

The particular catalyst employed in the process of the invention depends on the nature of the starting substrate.

When the starting ketone is to be reacted with an alkylating agent, i.e., there is no ester group in the α-position with respect to the carbonyl group, the catalyst selected is generally a trivalent rare earth orthophosphate having formula (IIIa).

When the ketone indeed has an ester group in the α-position with respect to the carbonyl group, the range of suitable catalysts is wider and any orthophosphate, dihydrogen phosphate, monohydrogen phosphate or condensed phosphate can be used, in particular trivalent rare earth orthophosphates of formula (III) and doped rare earth orthophosphates of formula (IIIa).

The C-alkylation reaction of this invention is carried out in the gas or liquid phase by contacting the starting ketone with the alkylating agent (if necessary), in the presence of a catalyst as described above.

The amount of alkylating agent employed is equal to or greater than the stoichiometric amount required to substitute one or more hydrogen atoms. By the term "more hydrogen atoms" is intended at most four hydrogen atoms per carbonyl group.

The alkylating agent is generally used in an amount such that the ratio between the number of moles of alkylating agent and the number of hydrogen atoms replaced by an alkyl group in a ketone ranges from 0.5 to 500, preferably from 1 to 10.

With respect to the catalyst, its hourly productivity by weight ranges from 0.1 to 20 $h^{-1}$, preferably from 1 to 5 $h^{-1}$; the hourly productivity by weight of a catalyst is defined as the weight ratio between the ketone introduced per hour and the catalyst.

The process of the invention can be carried out in the liquid or gaseous phase.

In a preferred first embodiment, the process of the invention is carried out in the gaseous phase By "gaseous phase" is intended that the reactants are vaporized under the reaction conditions, but the process does not exclude the presence of a liquid phase resulting either from the physical properties of the reactants, or from the use of pressure or of an organic solvent.

A vector gas is optional and is generally a gas or mixture of gases which does not react under the reaction conditions. Gases such as nitrogen, air, argon or helium may be used. Advantageously, the ratio by volume between the vector gas and the ketone ranges from 0 to 10, preferably from 0.1 to 2.0.

The temperature of the C-alkylation reaction generally ranges from 80° C. to 500° C., preferably from 200° C. to 350° C.

The reaction pressure advantageously ranges from $10^{-2}$ to 50 bars, and preferably is atmospheric pressure.

According to the process of the invention, the starting reactants, namely, the ketone and the alkylating agent, are vaporized and contacted with the catalyst, preferably entrained by a vector gas.

The contact time, defined as the ratio between the bulk volume of the catalyst and the gas stream flow rate (including the vector gas), can vary widely and most frequently ranges from 0.2 to 100 seconds. The contact time preferably ranges from 0.4 to 10 seconds.

Concerning practical operation of the process of the invention, a catalytic bed is prepared which comprises the active catalytic phase deposited onto a support (for example fritted glass) to permit the gases to circulate without eluting the catalyst. The reactants are then introduced; several variations are possible.

Each reactant, namely, the ketone and the alkylating agent, can be vaporized in separate chambers, then mixed in a mixing chamber and the resulting gas stream is contacted with the catalyst. The vector gas can be introduced in parallel to said gas stream, or introduced into the mixing chamber.

Another variation comprises preparing a solution of the ketone and alkylating agent, then vaporizing such mixture and contacting it with the catalyst in parallel with the vector gas.

In another embodiment, the ketone is melted by heating it to its melting point and a gas stream containing the alkylating agent and any water formed during the reaction is passed thereover. The stream becomes saturated in ketone and is then contacted with the catalyst.

In still another embodiment, an organic solvent is used which is inert under the reaction conditions and is selected to dissolve the ketone and the alkylating agent.

Preferably, an aprotic solvent having a high boiling point of greater than 80° C., preferably ranging from 80° C. to 300° C., is employed.

Exemplary such aprotic solvents include aliphatic or aromatic hydrocarbons such as hexane, heptane, cyclohexane, benzene, toluene or xylenes; chlorinated hydrocarbons such as dichlorobenzene; cyclic ethers such as tetrahydrofuran or dioxane; sulfones such as dimethylsulfoxide or sulfolane; cyclic carboxamides such as N-methylpyrrolidone; or aromatic nitriles such as benzonitrile.

A plurality of solvents can also be employed.

The amount of ketone used in the solvent is generally such that the solvent/ketone molar ratio ranges from 0 to 20, preferably from 0 to 5.

Thus, an organic solution containing the ketone and the alkylation agent is prepared which is then vaporized and contacted with the catalyst in parallel with the vector gas.

When the reaction is over, the gases are condensed together and the unreacted reactants are separated from the products by fractional distillation or crystallization. They may also be separated by fractional condensation.

Yet another embodiment of the invention comprises conducting the reaction in the liquid phase, optionally in the presence of an organic solvent.

The reactants, in particular the alkylating agent, can be employed as the reaction solvent, but an organic solvent may also be used.

The organic solvent must satisfy a number of requirements.

It must be stable under the conditions of reaction and inert with respect to the reactants and products obtained.

It must have a high boiling point, preferably ranging from 200° C. to 500° C.

Examples of particularly suitable solvents are:

(a) aliphatic and/or aromatic hydrocarbons, more particularly paraffins such as decane, undecane dodecane or tetradecane; aromatic hydrocarbons such as xylenes, cumene or petroleum cuts constituted by a mixture of alkylbenzenes, in particular Solvesso® type cuts;

(b) ethers, more particularly aromatic ethers such as biphenyl oxide and/or benzyl oxide;

(c) paraffin and/or naphthalene oils which are petroleum distillation residues.

A mixture of organic solvents can also be employed.

The process of the invention thus features the starting ketone, the alkylating agent if required, the catalyst for the reaction in the amounts described above, and the organic solvent.

The ketone concentration in the reaction medium generally ranges from 10% to 50% by weight thereof.

The reactants are introduced or charged into an autoclave in any order, then heated.

The C-alkylation reaction temperature generally ranges from 80° C. to 500° C., preferably from 200° C. to 350° C.

The pressure of the reaction advantageously ranges from 1 to 50 bars, preferably from 1 to 10 bars.

When the reaction is complete, the ketone is recovered via conventional techniques, in particular by distillation, decantation or crystallization.

In a preferred embodiment of the invention, a cyclic ketone is prepared containing 1 or 2 alkyl groups R' in the α-position with respect to the carbonyl group and having the following formula (IV):

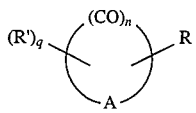

wherein A represents the residue of a cyclopentane or cyclohexane ring; R is a hydrogen atom, a linear or branched alkyl or alkoxy radical having from 1 to 6 carbon atoms, preferably 1 to 4 carbon atoms, or a benzylidene radical which is optionally halogenated; R' is a linear or branched alkyl radical having from 1 to 6 carbon atoms, preferably 1 to 4 carbon atoms; n equals 1; and g is a number ranging from 1 to 4, preferably 1 or 2.

The process according to the invention is particularly well suited for the preparation of 2-methylcyclopentanone from cyclopentanone or 2-methyl-2-carboxymethylcyclopentanone; or of 2,2-dimethylcyclopentanone from cyclopentanone and/or 2-methylcyclopentanone or 2-methyl-2-carboxymethylcyclopentanone.

It is also well suited for the preparation of 2,2-dimethyl-5-[(p-chloro)-benzylidene]cyclopentanone from 2-[(p-chloro)-benzylidene]cyclopentanone or 2-methyl-2-carboxymethyl-5-[(p-chloro)benzylidene]cyclopentanone.

In order to further illustrate the present invention and the advantages thereof, the following specific examples are given, it being understood that same are intended only as illustrative and in nowise limitative.

In said examples to follow, the abbreviations TR, AY and S have the following definitions:

$$\text{Transformation ratio} = TR = \frac{\text{number of moles of ketone transformed}}{\text{number of moles of ketone introduced}}, \%$$

$$\text{Actual Yield} = AY = \frac{\text{number of moles of C-alkylated ketone formed}}{\text{number of moles of ketone introduced}}, \%$$

$$\text{Selectivity} = S = \frac{\text{number of moles of C-alkylated ketone formed}}{\text{number of moles of ketone transformed}}, \%$$

EXAMPLE 1

106 g of $H_3PO_4$ (85%, marketed by PROLABO), i.e., 0.92 mole, were introduced into 800 ml of deionized water.

This solution was stirred at 500–700 rpm.

299 g of cold $La_2(CO_3)_3 \cdot 12H_2O$ (i.e., 0.8 mole of lanthanum in 736 ml of water) were introduced with vigorous stirring.

The reaction medium was then heated to 80° C. for two and one-half hours.

The medium was permitted to cool to room temperature without stirring for one-half hour, in a cold water bath.

The suspension was filtered through No. 3 fritted glass to remove the mother liquor.

The product was then redispersed in 2 liters of water with vigorous stirring and maintained in suspension for one-half hour, while maintaining the stirring.

The suspension was then filtered through No. 3 fritted glass to remove the mother liquor.

The product was redispersed in 900 ml of deionized water and neutralized with an aqueous ammonia solution to a pH of 9.

The product was filtered, washed with water and centrifuged before drying at 110° C.

The product was then calcined at 700° C. for 3 hours.

EXAMPLE 2

5 ml of quartz, 0.5 ml of lanthanum phosphate catalyst as prepared on Example 1 and an additional 5 ml of quartz were introduced into a Pyrex tubular reactor having a volume of 20 ml.

Nitrogen was introduced overhead using a flow meter, in parallel with a mixture of 2.01 g of 2-methylcyclopentanone (MCP) in solution in dimethylcarbonate (DMC) by means of a syringe; the dimethylcarbonate/2-methylcyclopentanone molar ratio was 3.

The gaseous effluents were condensed at the outlet of the reactor in a trap cooled in an ice-water bath. The condensates were diluted and then analyzed by gas phase chromatography.

The reaction was carried out at a nitrogen flow of 2 l/h and a solution supply rate of 1.98 ml/h.

After 1 hour of reaction at 250° C., the following results were obtained:

(a) $TR_{2\text{-methylcyclopentanone}} = 32.6\%$ (b) $S_{2,2\text{-dimethylcyclopentanone}} = 36.8\%$ (c) $S_{2,2,5\text{-trimethylcyclopentanone (TMCP)}} = 16\%$

EXAMPLE 3

182.4 g of $H_3PO_4$ (85%, marketed by PROLABO), i.e., 1.6 mole, in 640 ml of water, were introduced into a reactor.

The reaction medium was heated to 85° C. and when that temperature had been attained, 260.8 g of $La_2O_3$ (i.e., 0.8 mole of lanthanum) were introduced at regular intervals (14 g every 5 minutes).

The reaction mixture was heated for 1 hour at 85° C., then permitted to cool to room temperature without stirring.

The product was recovered by centrifugation (3,600 rpm), then redispersed in 400 ml of deionized water.

The washed product was recovered by centrifuging.

The washing operation was carried out 3 times, following the same procedure.

The washed product was then dried at 110° C.

The product was then calcined at 700° C. for 3 hours.

EXAMPLES 4 to 10

2,2-Dimethylcyclopentanone was prepared as in Example 2, using the catalyst described in Example 3.

The results obtained are reported in the following Table I:

TABLE I

| Example | Temperature (°C.) | Catalyst volume (ml) | Quantity DMC + MCP (g) | Molar ratio DMC/MCP | TR (%) | S DMCP (%) | S TMCP (%) |
|---|---|---|---|---|---|---|---|
| 4 | 350 | 0.5* | 2.06 | 3 | 44.9 | 42.7 | 23.3 |
| 5 | 250 | 0.5 | 2.41 | 3 | 47.2 | 43.4 | 23 |
| 6 | 200 | 0.5 | 2.30 | 3 | 13.6 | 31.6 | trace |
| 7 | 250** | 0.5 | 2.20 | 10 | 81.3 | 28 | 30 |
| 8 | 300 | 0.5 | 2.70 | 3 | 60.6 | 30.4 | 20 |
| 9 | 250 | 1.4 | 2.09 | 3 | 70.7 | 30.6 | 18.5 |
| 10 | 350 | 0.5 | 2.12 | 3 | 71.4 | 27.6 | 14.7 |

\* = catalyst prepared as in Example 3, but calcined at 550° C. overnight.
\*\* = presence of 2,2,5-tetramethylcyclopentanone: S = 25%.

EXAMPLES 11 to 16

2,2-Dimethylcyclopentanone was prepared under the conditions described in Example 2. Different results were obtained using different catalysts, as reported in the Table II which follows:

TABLE II

| Example | Temperature (°C.) | Catalyst (0.5 ml) | Quantity DMC + MCP (g) | Molar ratio DMC/MCP | TR (%) | S DMCP (%) | S TMCP (%) |
|---|---|---|---|---|---|---|---|
| 11 | 250 | $SmPO_4$ | 2.03 | 3 | 33 | 57.1 | 15 |
| 12 | 250 | $NdPO_4$ | 2.26 | 3 | 42.6 | 46.7 | 15 |
| 13 | 250 | $YPO_4$ | 2.36 | 3 | 32 | 21.8 | 8.4 |
| 14 | 350 | $YPO_4$ | 2.20 | 3 | 82.8 | 9 | 9.2 |
| 15 | 250 | $ErPO_4$ | 2.20 | 3 | 34 | 29.7 | 13.5 |
| 16 | 250 | $YbPO_4$ | 2.18 | 3 | 30.6 | 31.4 | 13.4 |

EXAMPLE 17

2,2-Dimethylcyclopentanone was prepared from cyclopentanone as described in Example 2, using the catalyst from Example 3.

A mixture of 2.22 g of cyclopentanone in solution in dimethylcarbonate (DMC) was used; the dimethylcarbonate/cyclopentanone ratio was 6.

After 1 hour at 250° C., the results obtained were as follows:

(a) $TR_{cyclopentanone}$=55.8%

(b) $AY_{2-methylcyclopentanone}$=21.7%

(c) $AY_{2,2-dimethylcyclopentanone}$=9.9%

(d) $AY_{2,2,5-trimethylcyclopentanone}$=6.7%

(e) $S_{2-methylcyclopentanone}$=38.9%

(f) $S_{2,2-dimethylcyclopentanone}$=17.7%

(g) $S_{2,2,5-trimethylcyclopentanone}$=12%

EXAMPLE 18

5 ml of quartz, 0.5 ml of lanthanum phosphate catalyst as prepared in Example 1 and an additional 5 ml of quartz were introduced into a Pyrex tubular reactor having a volume of 20 ml.

Nitrogen was introduced overhead using a flow meter, in parallel with a mixture of 2.49 g of 2-(p-chlorobenzylidene)cyclopentanone (BCP) in solution in dimethylcarbonate (DMC) by means of a syringe; the DMC/BCP molar ratio was 20.

The gaseous effluents were condensed at the outlet of the reactor in a trap cooled in an ice-water bath. The condensates were diluted and then analyzed by gas phase chromatography.

The reaction was carried out at a nitrogen flow of 2 l/h and a solution supply rate of 1.98 ml/h.

After 1 hour of reaction at 350° C., the following results were obtained:

(a) $TR_{BCP}$=100%

(b) $AY_{2,2-dimethyl-5-(p-chlorobenzylidene)cyclopentanone}$=4.02%

(c) $S_{2,2-dimethyl-5-(p-chlorobenzylidene)cyclopentanone}$=4.02%

EXAMPLES 19 to 21

2,2-Dimethyl-5-(p-chlorobenzylidene)cyclopentanone was prepared as in Example 18, using the catalyst of Example 3.

The results obtained are reported in the following Table III:

TABLE III

| Example | Temperature (°C.) | Contact time (s) | Quantity DMC + BCP (g) | Molar ratio DMC/BCP | TR (%) | AY (%) | S (%) |
|---|---|---|---|---|---|---|---|
| 19 | 250 | 0.8 | 1.79 | 20 | 66 | 35 | 53 |
| 20 | 250 | 0.4 | 2.69 | 20 | 38.1 | 12 | 31.5 |
| 21 | 250 | 1.2 | 2.14 | 20 | 91 | 17.6 | 19.4 |

EXAMPLE 22

4 g of BCP, 2 g of lanthanum phosphate prepared as described in Example 1 and 17.44 g of dimethylcarbonate were successively introduced into a stainless steel autoclave having a volume of 125 ml, under an argon atmosphere.

The autoclave was sealed and stirred for 4 h at 200° C. The DMC/BCP molar ratio was 10.

At the end of the reaction, the reaction mixture was diluted with dichloromethane in a volumetric flask and then analyzed via gas phase chromatography.

The following results were obtained:

(a) $TR_{BCP}=64\%$ (b) $AY_{2,2\text{-}dimethyl\text{-}5\text{-}(p\text{-}chlorobenzylidene)cyclopentanone}=15\%$ (c) $S_{2,2\text{-}dimethyl\text{-}5\text{-}(p\text{-}chlorobenzylidene)cyclopentanone}=23.4\%$

EXAMPLE 23

5 ml of quartz, 0.5 ml of lanthanum phosphate catalyst as prepared in Example 1 and an additional 5 ml of quartz were introduced into a Pyrex tubular reactor having a volume of 20 ml.

Nitrogen was introduced overhead using a flow meter, in parallel with a mixture of 2.35 g of 2-methyl-2-carboxymethylcyclopentanone (MCMCP) in solution in dimethylcarbonate (DMC) by means of a syringe; the dimethylcarbonate/MCMCP molar ratio was 3.

The gaseous effluents were condensed at the outlet of the reactor in a trap cooled in an ice-water bath. The condensates were diluted and then analyzed by gas phase chromatography.

The reaction was carried out at a nitrogen flow of 2 l/h and a solution supply rate of 1.98 ml/h.

After 1 hour of reaction at 250° C., the following results were obtained:

(a) $TR_{MCMCP}=25.5\%$ (b) $AY_{2\text{-}methylcyclopentanone}=47.4\%$ (c) $AY_{2,2\text{-}dimethylcyclopentanone}=12.1\%$

EXAMPLE 24

A catalyst based on lanthanum phosphate doped with cesium was prepared.

14.12 ml of a 1M aqueous solution of $H_3PO_4$ were added to 4.7 ml of a 6M aqueous solution of CsOH. A sufficient amount of water was then added to adjust the volume to 50 ml.

50 g of the product prepared in Example 1 were introduced into a 200 ml beaker.

20 ml of impregnating solution were added dropwise, while crushing and homogenizing the agglomerates formed.

The product remained as such for one hour. It was dried overnight at 110° C. and then calcined for 2 hours at 500° C.

Dry cesium content=3%.

EXAMPLES 25 to 39

2,2-Dimethylcyclopentanone was prepared as described in Example 23, without the addition of dimethylcarbonate.

The following Table IV results were obtained using different catalysts and operating conditions:

TABLE IV

| Example | Temperature (°C.) | Catalyst (0.5 ml) | Contact time (s) | Quantity MCMCP (g) | TR (%) | S MCP (%) | S DMCP (%) | S TMCP (%) |
|---|---|---|---|---|---|---|---|---|
| 25 | 350 | LaPO$_4$ | 0.8 | 2.35 | 88.8 | 30.6 | 22.5 | 12.7 |
| 26 | 350 | LaPO$_4$ | 0.4 | 2.34 | 83.4 | 19.7 | 16.3 | 7 |
| 27 | 350 | LaPO$_4$ | 1 | 2.35 | 88 | 38 | 28 | 14 |
| 28 | 300 | LaPO$_4$ | 0.8 | 2.16 | 39 | 48 | 18 | — |
| 29 | 400 | LaPO$_4$ | 0.8 | 2.17 | 100 | 29.3 | 20.1 | 12.2 |
| 30 | 250 | NdPO$_4$ | 0.8 | 1.39 | 67 | 20.4 | 12.5 | 5.4 |
| 31 | 350 | YbPO$_4$ | 0.8 | 1.16 | 93 | 31.8 | 9.8 | 10.3 |
| 32 | 350 | ErPO$_4$ | 0.8 | 1.26 | 93.6 | 28.5 | 15.1 | 4.8 |
| 33 | 350 | YPO$_4$ | 0.8 | 1.43 | 96 | 24.3 | 17 | 17.9 |
| 34 | 350 | AlPO$_4$ | 0.8 | 1.1 | 63.3 | 30.9 | 15.8 | 7.1 |
| 35 | 350 | SmPO$_4$ | 0.8 | 1.43 | 93.5 | 37.6 | 21.7 | 8.3 |
| 36 | 350 | CaHPO$_4$ | 0.8 | 1.93 | 25.4 | 15.7 | 23.2 | — |
| 37* | 350 | LaPO$_4$/Cs | 0.8 | 1.43 | 40.3 | 40.2 | 20.6 | 7.7 |
| 38 | 350 | BiPO$_4$ | 0.8 | 1.7 | 8.7 | 5.7 | — | — |
| 39 | 350 | Zr(HPO$_4$) | 0.8 | 1.4 | 14.2 | 35.9 | — | — |

\* = catalyst prepared as in Example 24.

EXAMPLE 40

5 ml of quartz, 0.5 ml of lanthanum phosphate catalyst as prepared in Example 1 and an additional 5 ml of quartz were introduced into a Pyrex tubular reactor having a volume of 20 ml.

Nitrogen was introduced overhead using a flow meter, in parallel with 2.0 g of 2-methyl-2-carboxymethyl-5-(p-chlorobenzylidene)cyclopentanone (MCMBCP) in solution in 4 ml of toluene by means of a syringe.

The gaseous effluents were condensed at the outlet of the reactor in a trap cooled in an ice-water bath. The condensates were diluted and then analyzed by gas phase chromatography.

The reaction was carried out at a nitrogen flow of 2 l/h and a solution supply rate of 1.98 ml/h.

After 1 hour of reaction at 350° C., the following results were obtained:

(a) $TR_{MCMBCP}=100\%$ (b) $AY_{2,2\text{-}dimethyl\text{-}5\text{-}(p\text{-}chlorobenzylidene)cyclopentanone}=47.0\%$

EXAMPLE 41

2,2-Dimethyl-5-(p-chlorobenzylidene)cyclopentanone was prepared as described in Example 40 using samarium phosphate as the catalyst. Under these conditions, the following results were obtained:

(a) $TR_{MCMBCP}=100\%$ (b) $AY_{2,2\text{-}dimethyl\text{-}5\text{-}chlorobenzylidene)cyclopentanone}=23\%$

EXAMPLE 42

5 ml of quartz, 0.5 ml of lanthanum phosphate catalyst as prepared in Example 1 and an additional 5 ml of quartz were introduced into a Pyrex tubular reactor having a volume of 20 ml.

Nitrogen was introduced overhead using a flow meter, in parallel with a mixture of 1.56 g of 3-pentanone in solution in dimethylcarbonate (DMC) by means of a syringe; the dimethylcarbonate/3-pentanone molar ratio was 3.

The gaseous effluents were condensed at the outlet of the reactor in a trap cooled in an ice-water bath. The condensates were diluted and then analyzed by gas phase chromatography.

The reaction was carried out at a nitrogen flow of 2 l/h and a solution supply rate of 1.98 ml/h.

After 1 hour of reaction at 250° C., the following results were obtained:

(a) $TR_{3\text{-}pentanone} = 41\%$ (b) $S_{2\text{-}methyl\text{-}3\text{-}pentanone} = 29\%$ While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An improved process for the preparation of a C- or α-alkylated ketone, comprising reacting a ketone having at least one hydrogen atom or ester group in the α-position with respect to a ketonic carbonyl group thereof, with an alkylating agent, in the presence of a catalyst, wherein the improvement comprises using as the catalyst a catalytically effective amount of a condensed or condensed catalyst which comprises a cationic moiety and an anionic moiety wherein the cationic moiety comprises a metal or ammonium and wherein the anionic moiety comprises an orthophosphate anion.

2. The process as defined by claim 1, said reactant ketone having at least one hydrogen atom in the α-position with respect to a ketonic carbonyl group thereof and wherein said condensed or uncondensed catalyst comprises a metallic or ammonium phosphate.

3. The process as defined by claim 1, said reactant ketone having at least one ester group in the α-position with respect to a ketonic carbonyl group thereof and wherein said condensed or uncondensed catalyst comprises a metallic or ammonium phosphate.

4. The process as defined by claim 3, said at least one ester group having the formula —$COOR_e$ in which $R_e$ is a linear or branched alkyl radical having from 1 to 6 carbon atoms.

5. The process as defined by claim 4, wherein said formula, $R_e$ is methyl or ethyl.

6. The process as defined by claim 1, said reactant ketone comprising at least two ketonic carbonyl groups.

7. The process as defined by claim 1, said reactant ketone comprising a cyclic ketone.

8. The process as defined by claim 1, said reactant ketone comprising a polycyclic ketone.

9. The process as defined by claim 8, said reactant ketone comprising a bicyclic ketone.

10. The process as defined by claim 1, said reactant ketone comprising a acyclic ketone.

11. The process as defined by claim 3, said at least one ester group in situ comprising said alkylating agent.

12. The process as defined by claim 7, said cyclic ketone having the general formula (Ia):

wherein A is a cyclic residue at least in part comprising a monocyclic or polycyclic ring system containing at least one ketonic carbonyl group and having at least one hydrogen atom or ester group in the α-position with respect to at least one ketonic carbonyl group; R is a hydrogen, or one or more inert substituents; and n is 1 or 2.

13. The process as defined by claim 12, wherein formula (Ia), A is the residue of a saturated or unsaturated monocyclic or carbocyclic compound; of a polycyclic compound comprising at least two saturated and/or unsaturated carbocycles; of a polycyclic compound comprising at least two saturated and/or unsaturated carbocycles, one or more of the carbon atoms of which being replaced by a heteroatom; or of a polycyclic compound comprising at least two carbocycles, one of which being aromatic.

14. The process as defined by claim 12, wherein formula (Ia), at least one substituent R is a substituent $R_0$, selected from among:

(a) a linear or branched acyclic aliphatic radical having from 1 to 20 carbon atoms, which may be saturated or unsaturated, the hydrocarbon chain of which may be interrupted by a Z group —O—, —CO—, COO—, —$NR_2$—, —CO—$NR_2$, —S—, or —$SO_2$— in which $R_2$ is a hydrogen atom, or a linear or branched alkyl radical having from 1 to 6 carbon atoms; and/or (b) one of the following groups —OH, —CN, —N[$R_2$]$_2$, —$COOR_2$, —$CF_3$ or —X in which the radicals $R_2$, which may be identical or different, are each a hydrogen atom or a linear or branched alkyl radical having from 1 to 6 carbon atoms and X is a halogen atom;

(c) an =$R_3$ radical in which $R_3$ is an alkylidene radical having from 1 to 6 carbon atoms, a radical having the formula =$C(CN)_2$ or a cycloalkylidene or cycloalkenylidene radical having 5 or 6 carbon atoms, or an optionally substituted benzylidene radical;

(d) a linear or branched alkoxy radical having from 1 to 6 carbon atoms;

(e) with the proviso that two successive atoms of the cycle may be joined together via an epoxy bridge or by an alkylenedioxy bridge having from 1 to 4 carbon atoms;

(f) an OH group;

(g) a $COOR_4$ group in which $R_4$ is a hydrogen atom or an alkyl radical having from 1 to 4 carbon atoms;

(h) a CN group;

(i) a halogen atom;

(j) a —$CF_3$ group; or

R is a substituent $R_1$ selected from among:

(a') a saturated or unsaturated carbocyclic radical having from 4 to 7 carbon atoms;

(b') a radical having the formula:

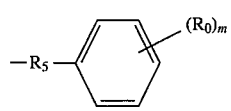

in which $R_5$ is a valence bond or a divalent, linear or branched, saturated or unsaturated divalent hydrocarbon radical having from 1 to 6 carbon atoms, $R_0$ is as defined above and m is a whole number ranging from 0 to 4;

(c') an $—R_5—Z—R_8$ radical in which Z and $R_5$ are as defined above, $R_8$ is a linear or branched alkyl radical having from 1 to 6 carbon atoms, or a radical having the formula:

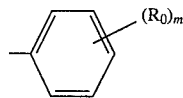

wherein $R_0$ and m are as defined above; or (d') a spiro radical having one of the formulae:

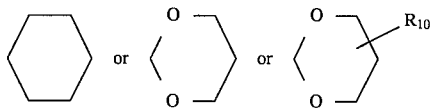

wherein $R_{10}$ is one or more linear or branched alkyl radicals having from 1 to 6 carbon atoms.

15. The process as defined by claim 1, said reactant ketone having the general formula (1b):

in which $R_{11}$ and $R_{12}$, which may be identical or different, are each a hydrocarbon radical having from 1 to 20 carbon atoms comprising a linear or branched, saturated or unsaturated aliphatic acyclic radical; a saturated or unsaturated, monocyclic or polycyclic, aromatic carbocyclic or heterocyclic radical; a linear or branched, saturated or unsaturated aliphatic radical substituted by at least one cyclic substituent, with the proviso that at least one of the radicals $R_{11}$ and $R_{12}$ contains a carbon atom in the α-position with respect to the ketonic carbonyl group which is substituted by at least one hydrogen atom or ester group.

16. The process as defined by claim 15, wherein formula (1b), $R_{11}$ and $R_{12}$ are each a linear or branched, saturated or unsaturated acyclic aliphatic radical.

17. The process as defined by claim 1, said reactant ketone comprising cyclobutanone, cyclopentanone, 2-methylcyclopentanone, 3-methylcyclopentanone, 2-methyl-2-carboxymethylcyclopentanone, 2,2-dimethylcyclopentanone, 2-(2-octenyl)-cyclopentanone, 2-(3,7-dimethyl-2,6-octadienyl)cyclopentanone, 2-cyclopentylidenecyclopentanone, 2-benzylidenecyclopentanone, 2-[(p-chloro)benzylidenelcyclopentanone, 2-methyl-2-carboxymethyl-5-[(p-chloro)benzylidene cyclopentanone, 2,4-dimethylcyclopentanone, 2,5-dimethylcyclopentanone, 3,4-dimethylcyclopentanone, 2,2,4-trimethylcyclopentanone, 5-methyl-2-(1-methylethylidene)cyclohexanone, 6-ketoprostaglandin E1, methylester prostaglandin E2, prostaglandin D2, cyclohexanone, 3-methylcyclohexanone, 4-n-pentylcyclohexanone, 2-(n,n-dimethylamino)cyclohexanone, 3,5-dimethylcyclohexanone, dihydrocarvone, cycloheptanone, cyclooctanone, or cycloheptadecanone.

18. The process as defined by claim 1, said reactant ketone comprising 1,3-cyclopentanedione, 2-allyl-2-methyl-1,3-cyclopentanedione, 3,3-dimethyl-1,2-cyclopentanedione, 3,4-dimethyl-1,2-cyclopentanedione, 1,2-cyclohexanedione, 1,3-cyclohexanedione, 1,4-cyclohexanedione, or 1,2-cycloheptanedione.

19. The process as defined by claim 1, said reactant ketone comprising 2-cyclopentenone, 3-methyl-2-cyclopentenone, 4,4-dimethyl-2-cyclopentenone, 2-pentyl-2-cyclopentenone, 3-ethoxy-2-cyclopentenone, 2-hydroxy-3-ethyl-2-cyclopentenone, prostaglandin J2, jasmone, 2-hydroxy-3,4-dimethyl-2-cyclopentenone, 15-oxoprostaglandin E2, 2-ethoxy-2-cyclohexenone, 3-bromo-2-cyclohexenone, carvone, 8-hydroxycarvotanacetone, 2-methyl-5-(1-methylethenyl)-2-cyclohexenone, 3,5,5-trimethyl-2-cyclohexenone, methyl ester of abscisic acid, 2-hydroxy-3-methyl-6-(1-methylethyl)-2-cyclohexenone, or 5-cyclohexadecenone.

20. The process as defined by claim 1, said reactant ketone comprising 2-cyclopentene-1,4-dione, or 4-hydroxy-5-methyl-4-cyclopentene-1,3-dione.

21. The process as defined by claim 1, said reactant ketone comprising camphor, norcamphor, 3-bromocamphor, 2,3-bornanedione, 1-decalone, 2-decalone, or n-(ethoxycarbonyl)nortropinone.

22. The process as defined by claim 1, said reactant ketone comprising bicyclo[3.2.0]hept-2-en-6-one, 1-(methoxymethyl)-bicyclo[2.2.0]hept-5-en-2-one, or 3,4,8,8a-tetrahydro-8a-methyl-1,6(2h,7h)naphthalenedione.

23. The process as defined by claim 1, said reactant ketone comprising 6,7-dihydro-cyclopenta-1,3-dioxin-5(4H)one, 6,7-dihydro-1,1,2,3,3-pentamethyl-4(5h) indanone, or 4-oxo-4,5,6,7-tetrahydroindole.

24. The process as defined by claim 1, said reactant ketone comprising 2-indanone, 2-methyl-1-indanone, 4-methyl-1-indanone, 4-methoxy-1-indanone, 6-methoxy-1-indanone, 4-hydroxy-1-indanone, 5-bromo-1-indanone, 1,3-indanedione, 1-tetralone, 2-tetralone, 4-methyl-1-tetralone, 5,7-dimethyl-1-tetralone, 5-methoxy-1-tetralone, 6,7-dimethoxy-1-tetralone, 5-hydroxy-1-tetralone, or levobunolol.

25. The process as defined by claim 1, said reactant ketone comprising acetone, methylethylketone, methylisopropylketone, methylisobutylketone, 2-pentanone, 3-pentanone, 2-carboxymethyl-3-pentanone, 2-hexanone, 3-hexanone, 5-methyl-2-hexanone, 2-heptanone, 3-heptanone, 4-heptanone, 2-octanone, 3-octanone, diisobutylketone, 5-methyl-2-octanone, 2-nonanone, or 2,6,8-trimethyl-4-nonanone.

26. The process as defined by claim 1, said reactant ketone comprising 1,3-dihydroxy-2-propanone, diacetone alcohol, triacetone alcohol, or 4-methoxy-4-methyl-2-pentanone.

27. The process as defined by claim 1, said reactant ketone comprising mesityl oxide, 3-butene-2-one, or 4-methyl-4-pentene-2-one.

28. The process as defined by claim 1, said reactant ketone comprising 2,3-pentanedione, 2,3-hexanedione, 3,4-hexanedione, 4-methyl-2,3-pentanedione, 3,4-heptanedione, 5-methyl-2,3-hexanedione, 2,3-octanedione, 4,5-octanedione, 2,5-dimethyl-3,4-hexanedione, 5-methyl-3,4-heptanedione, 6-methyl-3,4-heptanedione 1-phenyl-1,2-propanedione, 2,4-pentanedione, 2,4-hexanedione, 2,4-heptanedione, 1-phenyl-1,3-butanedione, 1-phenyl-1,3-pentanedione, 1,3-diphenyl -1,3-propanedione, 1-phenyl-2,4-pentanedione, 2,5-hexanedione, 3,4-dimethyl-2,5-hexanedione, 3,3,4,4-tetramethyl-2,5-hexanedione, 2,5-heptanedione, 3,6-octanedione, 6-methyl-2,5-heptanedione, 2,5-decanedione, 2,5-dodecanedione, or 1,4-diphenyl-1,4-butanedione.

29. The process as defined by claim 1, said reactant ketone comprising acetophenone, propiophenone, 2,2-diethoxyacetophenone, acetylpyrazine, 2-acetylpyridine, 3-acetylpyridine, 4-acetylpyridine, 2-acetylpyrrole, or 2-acetyl-1-tetralone.

30. The process as defined by claim 1, said reactant ketone comprising cyclopentanone or a substituted cyclopentanone.

31. The process as defined by claim 1, said alkylating agent having the following general formula (II):

$$[R_a-CO-O\frac{}{p}R_b \quad (II)$$

wherein $R_a$ is a radical $R_c$ comprising an optionally substituted hydrocarbon radical having from 1 to 12 carbon atoms and which comprises a linear or branched, saturated or unsaturated aliphatic radical; a monocyclic or polycyclic, saturated or unsaturated carbocyclic radical; or a linear or branched, saturated or unsaturated acyclic aliphatic radical bearing at least one cyclic substituent; an $R_d$—O—CO—$R_f$ radical in which $R_d$ is $R_c$ and $R_f$ is a simple valence bond or a linear or branched, saturated or unsaturated divalent aliphatic radical containing at least one carbon atom; an $R_d$—O— radical in which $R_d$ is $R_c$; or an $R_d$—O—CO—O— radical in which $R_d$ is $R_c$; $R_b$ is an $R_c$ radical, or an alkali or alkaline earth metal, with the proviso that $R_a$ and $R_b$ can together form a linear or branched, saturated or unsaturated divalent aliphatic radical having at least 2 carbon atoms; and p is a whole number equal to 1 or 2.

32. The process as defined by claim 1, said alkylating agent having the following general formula (IIa):

$$R_a-CO-O-R_b \quad (IIa)$$

wherein $R_a$ is a linear or branched alkyl radical having from 1 to 6 carbon atoms; a cycloalkyl radical having 5 or 6 carbon atoms; an aralkyl radical having from 7 to 12 carbon atoms; an $R_c$—O—CO—$R_d$ radical in which $R_c$ is $R_a$ and $R_d$ is a valence bond or an alkylene radical having from 1 to 6 carbon atoms; and $R_b$ is a linear or branched alkyl radical having from 1 to 6 carbon atoms, or a cycloalkyl radical having 5 or 6 carbon atoms, with the proviso that $R_a$ and $R_b$ may together form an alkylene radical having from 2 to 4 carbon atoms.

33. The process as defined by claim 1, said alkylating agent comprising an organic carbonate or mixed organometallic carbonate.

34. The process as defined by claim 1, said alkylating agent having the following general formula (IIb):

$$[R_a-O-CO-O\frac{}{p}R_b \quad (IIb)$$

wherein $R_a$ is a linear or branched, optionally substituted alkyl radical having from 1 to 6 carbon atoms, a cycloalkyl radical having 5 or 6 carbon atoms, an aryl radical having from 6 to 12 carbon atoms, an $R_d$—O—CO—$R_d$ radical in which $R_d$ is a linear or branched alkyl radical having from 1 to 6 carbon atoms or a cycloalkyl radical having 5 or 6 carbon atoms; $R_b$ is a linear or branched alkyl radical having from 1 to 6 carbon atoms, a cycloalkyl radical having 5 or 6 carbon atoms, or an alkali or alkaline earth metal; and p=1, or p=2 when $R_b$ is an alkaline earth metal; with the proviso that $R_a$ and $R_b$ may together form an alkylene radical having from 2 to 6 carbon atoms.

35. The process as defined by claim 1, said alkylating agent comprising a dialkylsulfate.

36. The process as defined by claim 1, said alkylating agent comprising an alcohol.

37. The process as defined by claim 1, said alkylating agent having the following general formula (IIc):

$$R_i-OH \quad (IIc)$$

wherein $R_i$ is a hydrocarbon radical having from 1 to 12 carbon atoms comprising a linear or branched, saturated or unsaturated acyclic aliphatic radical, a saturated or unsaturated, monocyclic or polycyclic cycloaliphatic radical, or a linear or branched, saturated or unsaturated aliphatic radical substituted by at least one cyclic substituent.

38. The process as defined by claim 1, said alkylating agent comprising an organic ester.

39. The process as defined by claim 37, said alkylating agent comprising methanol or ethanol.

40. The process as defined by claim 1, said metallic or ammonium phosphate catalyst comprising a dihydrogen phosphate, a monohydrogen phosphate, a phosphate, a pyrophosphate or a polyphosphate.

41. The process as defined by claim 1, said catalyst comprising an othophosphate of an element of Group 1a, 2a 3a or 3b of the Periodic Table.

42. The process as defined by claim 1, said catalyst comprising a phosphate, pyrophosphate, tripolyphosphates or pentapolyphosphate of sodium or potassium.

43. The process as defined by claim 1, said catalyst having the formula (III):

$$MPO_4 \quad (III)$$

wherein M is a trivalent rare earth.

44. The process as defined by claim 1, said catalyst having the formula (IIIa):

$$MPO_4(Im)_p \quad (IIIa)$$

wherein M is a trivalent rare earth $M_3$ or a mixture of at least one trivalent rare earth $M_3$ and at least one element selected from among the alkali metals $M_1$ and alkaline earth metals $M_2$ in the relationship:

$$M=\alpha M_1^+ + \beta M_2^{++} + \gamma M_3^{3+} \text{ and } \alpha+2\beta+3\gamma=3;$$

Im represents a basic impregnating compound comprising an alkaline earth metal, an alkali metal, or mixture thereof, associated with a counter-anion to provide electrical neutrality; $\alpha$ is a coefficient up to 3; $\beta$ is a coefficient ranging up to 3/2; $\gamma$ is a coefficient ranging up to 1; and p is less than 0.5.

45. The process as defined by claim 44, wherein formula (IIIa), $M_1$ is at least one element of Group 1a of the Periodic Table; $M_2$ is at least one element of Group 2a of the Periodic Table; and $M_3$ is at least one trivalent rare earth element.

46. The process as defined by claim 45, wherein formula (IIIa), $M_1$ is at least one of lithium, sodium, potassium, rubidium and cesium; $M_2$ is at least one of beryllium, magnesium, calcium, strontium and barium; and $M_3$ is at least one of lanthanum, cerium, praseodymium, neodymium, samarium, europium, gadolinium, terbium, dysprosium, holmium, erbium, thulium, ytterbium and lutetium.

47. The process as defined by claim 1, said catalyst comprising a trivalent rare earth metal doped with an alkali and/or an alkaline earth metal.

48. The process as defined by claim 1, said catalyst comprising sodium orthophosphate, potassium orthophosphate, aluminum orthophosphate, ammonium orthophosphate, silver orthophosphate, barium orthophosphate, calcium orthophosphate, chromium orthophosphate, cobalt orthophosphate, copper orthophosphate, magnesium ammonium orthophosphate, iron orthophosphate, lithium orthophosphate, magnesium orthophosphate, manganese orthophosphate, zinc orthophosphate, sodium monohydrogen phosphate, calcium monohydrogen phosphate, magnesium monohydrogen phosphate, zirconium monohydrogen phosphate, sodium pyrophosphate, potassium pyrophosphate, calcium pyrophosphate, copper pyrophosphate, zinc pyrophosphate, sodium pentapolyphosphate $Na_7P_5O_{16}$, sodium tripolyphosphate $Na_5P_3O_{10}$, or potassium tripolyphosphate $K_5P_3O_{10}$.

49. The process as defined by claim 1, carried out in gaseous phase.

50. The process as defined by claim 1, carried out in liquid phase.

51. The process as defined by claim 50, carried out in the presence of an inert organic solvent.

52. The process as defined by claim 51, wherein the reactant ketone concentration in the medium of reaction ranges from 10% to 50% by weight thereof.

53. The process as defined by claim 2, wherein the amount of alkylating agent is such that the ratio between the number of moles thereof to the number of hydrogen atoms replaced by an alkyl group ranges from 0.5 to 500.

54. The process as defined by claim 53, said ratio ranging from 1 to 10.

55. The process as defined by claim 1, wherein the hourly productivity by weight of said condensed or uncondensed orthophosphate catalyst ranges from 0.1 to 20 $h^{-1}$.

56. The process as defined by claim 1 carried out at a temperature ranging from 80° C. to 500° C.

* * * * *